United States Patent [19]

Nishiyama et al.

[11] 4,267,336
[45] May 12, 1981

[54] PROCESS FOR PRODUCING 4-(PYRIDYL-2-OXY)-PHENOXYALKANECARBOXYLIC ACID OR ITS DERIVATIVES

[75] Inventors: Ryuzo Nishiyama, Takatsuki; Kanichi Fujikawa, Moriyama; Rikuo Nasu, Kyoto; Itaru Shigehara, Moriyama, all of Japan

[73] Assignee: Ishihara Sangyo Kaisha Ltd., Osaka, Japan

[21] Appl. No.: 137,954

[22] Filed: Apr. 7, 1980

[30] Foreign Application Priority Data

Apr. 19, 1979 [JP] Japan .................................. 54/48147

[51] Int. Cl.³ ..................... A01N 9/22; C07D 213/57; C07D 213/64
[52] U.S. Cl. ................................................. 546/302
[58] Field of Search ........................................ 546/302

[56] References Cited

U.S. PATENT DOCUMENTS

| | | | |
|---|---|---|---|
| 4,046,553 | 9/1977 | Takahashi et al. | 546/302 X |
| 4,105,435 | 8/1978 | Nishiyama et al. | 546/302 X |
| 4,133,675 | 1/1979 | Schurter et al. | 546/302 X |
| 4,134,751 | 1/1979 | Nishiyama et al. | 546/302 X |

*Primary Examiner*—Joseph Paul Brust
*Attorney, Agent, or Firm*—Oblon, Fisher, Spivak, McClelland & Maier

[57] ABSTRACT

4-(Pyridyl-2-oxy)phenoxyalkanecarboxylic acid derivative is produced by reacting 2-phenoxypyridine derivative with 4-hydroxyphenoxyalkanecarboxylic acid derivative. The products which are effective as an active ingredient of a herbicide can be obtained at high yield by an interphenoxylation.

4 Claims, No Drawings

PROCESS FOR PRODUCING 4-(PYRIDYL-2-OXY)-PHENOXYALKANECARBOXYLIC ACID OR ITS DERIVATIVES

BACKGROUND OF THE INVENTION

1. Field of the Invention

The present invention relates to a process for producing 4-(pyridyl-2-oxy)phenoxyalkanecarboxylic acid or its derivatives.

2. Description of the Prior Arts

The 4-(pyridyl-2-oxy)phenoxyalkanecarboxylic acid or its derivatives are useful as selective herbicides for controlling gramineous weed in an up-land for broadleaf plants. Therefore, an industrial process for producing these compounds has been demanded.

SUMMARY OF THE INVENTION

The present invention is to provide a process for producing 4-(pyridyl-2-oxy)phenoxyalkanecarboxylic acid or its derivatives having the formula

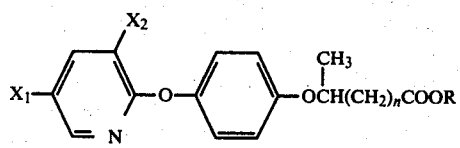

wherein $X_1$, $X_2$, R and n are defined below, which comprises reacting 2-phenoxypyridine derivative having the formula

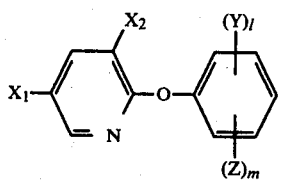

wherein $X_1$ represents a halogen atom or trifluoromethyl group; $X_2$ represents hydrogen atom or a halogen atom; Y represents methyl group; Z represents halogen atom; $l$ is 0 to 2 (integer); m is 0 to 5 (integer) and $l+m$ is an integer of 5 or less, with 4-hydroxyphenoxyalkanecarboxylic acid or its derivative having the formula

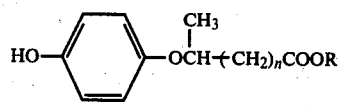

wherein R represents hydrogen atom, a lower alkyl group or a cation; and n is 0 or 2, in the presence of an alkaline compound.

DETAILED DESCRIPTION OF THE PREFERRED EMBODIMENTS

In the above-mentioned formulas, the halogen atom can be chlorine, bromine or fluorine atoms; and the lower alkyl group can be methyl, ethyl, n-propyl, isopropyl, n-butyl, isobutyl and tert-butyl group; and the cation can be sodium potassium, magnesium and calcium.

The alkaline compounds can be sodium hydroxide, potassium hydroxide, sodium carbonate and potassium carbonate.

The 2-phenoxypyridine derivative (I) as the reagent in the process of the present invention can be usually produced by the following process:

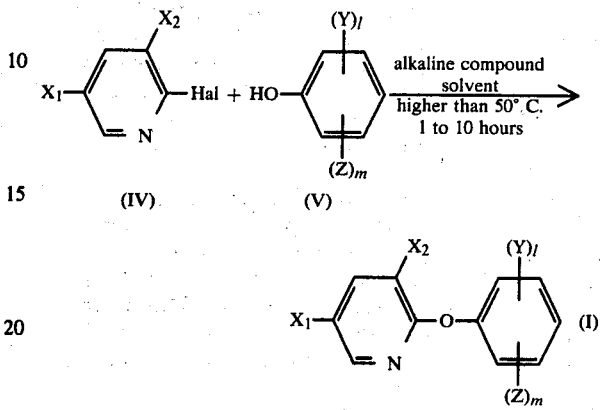

wherein Hal represents a halogen atom; and $X_1$, $X_2$, Y, Z, $l$ and m are defined above.

The alkaline compound used in the process can be sodium hydroxide, potassium hydroxide, sodium carbonate and potassium carbonate etc.

The solvent used in the process can be an aprotic polar solvent such as dimethylsulfoxide, dimethylformamide, hexamethylphosphoroamide and sulforane.

It is also possible to produce 2-phenoxypyridine derivative (I) by reacting 2,6-dichloro-3-trifluoromethyl pyridine instead of 2-halopyridine (IV), with the phenol derivative (V) to produce 2-phenoxy-6-chloropyridine derivative and selectively dechlorinating chlorine atom on the pyridine ring.

The 4-hydroxyphenoxyalkanecarboxylic acid or its derivatives as the other reagent in the process of the present invention can be usually produced by reacting hydroquinone with γ-valerolactone, α-halopropionic acid or its derivative in the presence of said alkaline compound and a solvent at 20° to 150° C.

In the process of the present invention, the reaction of said 2-phenoxypyridine derivative with said 4-hydroxyphenoxyalkanecarboxylic acid or its derivative is carried out in the presence of an alkaline compound. It is possible to carry out the process of the present invention by adding the 4-hydroxyphenoxyalkanecarboxylic acid or its derivative to 2-phenoxypyridine derivative as the reagent which is produced by reacting the 2-halopyridine (IV) with the phenol derivative (V) without separating the intermediate as a serial reaction.

The reaction of the present invention is usually carried out in the presence of a suitable amount of an aprotic polar solvent such as dimethylsulfoxide, dimethylformamide, hexamethylphosphoroamide and sulforane.

The reagent and the alkaline compound are usually used at a molar ratio of the 4-hydroxyphenoxyalkanecarboxylic acid or its derivative to the 2-phenoxypyridine derivative of 1 to 1.5 preferably 1.1 to 1.2, and a molar ratio of the alkaline compound to the 2-phenoxypyridine derivative of 1 to 2 preferably 1.1 to 1.4.

The reaction is usually carried out at a reaction temperature of 50° C. to the refluxing temperature; preferably 70° to 120° C. for a reaction time of 0.5 to 10 hours preferably 1 to 5 hours. In the reaction, the object product, 4-(pyridyl-2-oxy)phenoxyalkanecarboxylic acid or its derivative is produced together with the phenol derivative (V). These compounds are contained together with the unreacted reagents and by-products in the reaction mixture. The reaction product is purified by the conventional process such as a distillation, an extraction, a crystallization and a washing to obtain the object product, 4-(pyridyl-2-oxy)phenoxyalkanecarboxylic acid or its derivative at high yield. The phenol derivative (V) produced in the reaction is separated and reused for the reaction with the 2-halopyridine so as to convert it into the 2-phenoxypyridine derivative as the reagent.

Suitable 2-phenoxypyridine derivatives are compounds having the formula (I) wherein $X_1$ represents trifluoromethyl group; $X_2$ represents hydrogen or chlorine atom; Z represents chlorine atom and Y, l and m are defined above; preferably $X_1$ represents trifluoromethyl group; $X_2$ represents hydrogen atom, Z represents chlorine atom; l is 0 and m is an integer of 1 to 5 and Y is defined above.

Suitable 4-hydroxyphenoxyalkanecarboxylic acid or its derivatives are compound having the formula (II) wherein n is 0 and R is defined above.

The alkaline compounds used in the process of the present invention can be alkali metals, alkali metal hydroxides and alkali metal carbonates such as sodium, sodium hydroxide, potassium hydroxide, sodium carbonate and potassium carbonate, and especially alkali metal hydroxides and alkali metal carbonates.

The present invention will be further illustrated by certain examples, however it is not limited by the description of the examples.

EXAMPLE 1

Into 8 ml. of dimethylsulfoxide, 5.4 g. of 2-chloro-5-trifluoromethylpyridine and 5.4 g. of 2,4-dichlorophenol were dissolved and a reaction was carried out in the presence of 2 g. of potassium hydroxide at 110° C. for 3 hours. The product was purified by an extraction, a washing and a drying to obtain 7.5 g. of 2-(2,4-dichlorophenoxy)-5-trifluoromethylpyridine having a boiling point of 134° to 136° C./3 mmHg.

Into 6 ml. of dimethylsulfoxide, 1.4 g. of α-(4-hydroxyphenoxy)propionic acid was dissolved and then 1.2 g. of potassium hydroxide was added and 2 g. of 2-(2,4-dichlorophenoxy)-5-trifluoromethylpyridine was added dropwise. The reaction was carried out at 100° C. for 4 hours. Into the reaction mixture, 20 ml. of water was added and the mixture was acidified with sulfuric acid and extracted with ethyl ether. Ether was distilled off and 2,4-dichlorophenol was distilled off by a steam distillation and then the product was extracted with toluene and recrystallized from a mixed solvent of toluene-n-hexane to obtain 1.3 g. of α-[4-(5-trifluoromethylpyridyl-2-oxy)-phenoxy]propionic acid having a melting point of 102° to 103° C.

EXAMPLE 2

Into 7 ml. of dimethylsulfoxide, 2.6 g. of n-butyl α-(4-hydroxyphenoxy)propionate, 1.8 g. of potassium carbonate anhydrate and 2.5 g. of 2-(2,4-dichlorophenoxy)-5-trifluoromethylpyridine. The reaction was carried out at 100° C. for 3 hours. The reaction mixture was poured into water and extracted with methylenechloride and washed with water. Methylenechloride was distilled off and then 2,4-dichlorophenol was distilled off under a reduced pressure to obtain 1.0 g. of n-butyl α-[4-(5-trifluoromethylpyridyl-2-oxy)phenoxy]propionate having a boiling point of 165° to 170° C./2 mmHg.

EXAMPLE 3

In accordance with the process of Example 1 except using 1.5 g. of γ-(4-hydroxyphenoxy) valeric acid instead of 1.4 g. of α-(4-hydroxyphenoxy)propionic acid, the reaction was carried out and the purification was carried out to obtain 1.7 g. of γ-[4-(5-trifluoromethylpyridyl-2-oxy)phenoxy]valeric acid having a melting point of 231° to 235° C.

EXAMPLE 4

In accordance with the process of the production of 2-(2,4-dichlorophenoxy)-5-trifluoromethylpyridine of Example 1, 18 g. of 2-chloro-5-trifluoromethylpyridine and 10.8 g. of phenol were reacted to obtain 22 g. of 2-phenoxy-5-trifluoromethylpyridine having a boiling point of 97° to 101° C./2 mmHg.

Into 6 ml. of dimethylsulfoxide, 2.2 g. of α-(4-hydroxyphenoxy)propionic acid, 1.8 g. of potassium hydroxide and 2.4 g. of 2-phenoxy-5-trifluoromethylpyridine were added. The reaction was carried out at 100° C. for 3.5 hours. The reaction mixture was poured into water and acidified, extracted with toluene and washed with water. Toluene and phenol were distilled off and recrystallized to obtain 1.8 g. of α-[4-(5-trifluoromethylpyridyl-2-oxy)phenoxy]propionic acid.

EXAMPLE 5

In accordance with the process of the production of 2-(2,4-dichlorophenoxy)-5-trifluoromethylpyridine of Example 1, 18.2 g. of 2-chloro-5-trifluoromethylpyridine and 11.5 g. of p-cresol were reacted to obtain 23 g. of 2-(4-methylphenoxy)-5-trifluoromethylpyridine having a boiling point of 106° to 108° C./4 mmHg.

Into 6 ml. of dimethylsulfoxide, 1.8 g. of α-(4-hydroxyphenoxy)propionic acid, 1.5 g. of potassium hydroxide and 2.5 g. of 2-(4-methylphenoxy)-5-trifluoromethylpyridine were added. The reaction was carried out at 100° C. for 4 hours and the product was purified as the process of Example 4 to obtain 1.5 g. of α-[4-(5-trifluoromethylpyridyl-2-oxy)phenoxy]propionic acid.

EXAMPLE 6

Into 50 ml. of dimethylsulfoxide, 15.3 g. of 2-chloro-5-trifluoromethylpyridine, 13.1 g. of p-chlorophenol and 6.1 g. of potassium hydroxide were added. The reaction was carried out at 70° to 80° C. for 2 hours.

The elimination of 2-chloro-5-trifluoromethylpyridine and the production of 2-(4-chlorophenoxy)-5-trifluoromethylpyridine were confirmed by a gas chromatography.

Into the reaction mixture, 14.5 g. of potassium hydroxide and 22 g. of α-(4-hydroxyphenoxy)propionic acid were added. The reaction was carried out at 110°–120° C. for 3 hours. The reaction product was purified by the process of Example 1 to obtain 22 g. of α-[4-(5-trifluoromethylpyridyl-2-oxy)phenoxy]propionic acid.

EXAMPLE 7

In accordance with the process of Example 1, each reaction of each 2-phenoxypyridine derivative and each 4-hydroxyphenoxyalkanecarboxylic acid shown in Table was carried out. As a result, the corresponding 4-(pyridyl-2-oxy)phenoxyalkanecarboxylic acid or its derivative was obtained at substantially same yield.

TABLE

| No. | 2-phenoxypyridine derivative | 4-hydroxyphenoxyalkanecarboxylic acid, or derivative | 4-(pyridyl-2-oxy)phenoxyalkanecarboxylic acid or derivative |
|---|---|---|---|
| 1 | 2-(2,4-dichlorophenoxy)-5-trifluoromethylpyridine (3 g.) | ethyl$\alpha$-(4-hydroxyphenoxy)propionate (2.5 g.) | ethyl$\alpha$-[4-(5-trifluoromethylpyridyl-2-oxy)phenoxy]propionate (2.3 g.) |
| 2 | 2-phenoxy-3-chloro-5-trifluoro-methylpyridine (2.7 g.) | $\alpha$-(4-hydroxyphenoxy)propionic acid (2.3 g.) | $\alpha$-[4-(3-chloro-5-trifluoromethyl]-pyridyl-2-oxy)-phenoxy]propionic acid (1.8 g.) |
| 3 | 2-(2,4,6-trichlorophenoxy)-3,5-dichloropyridine (3.4 g.) | $\alpha$-(4-hydroxyphenoxy)propionic acid (2.2 g.) | $\alpha$-[4-(3,5-dichloropyridyl-2-oxy)phenoxy]-propionic acid (2.8 g.) |

We claim:

1. A process for producing 4-(pyridyl-2-oxy) phenoxyalkanecarboxylic acid or its derivative having the formula

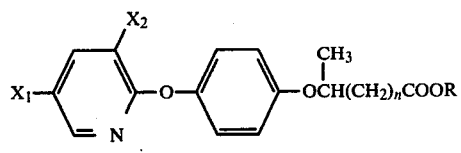  (III)

wherein $X_1$, $X_2$, R and n are defined below, which comprises reacting 2-phenoxypyridine derivative having the formula

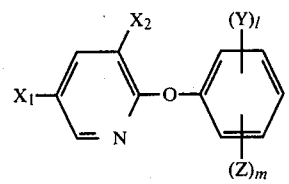  (I)

wherein $X_1$ represents a halogen atom or trifluoromethyl group; $X_2$ represents hydrogen or a halogen atom; Y represents methyl group; Z represents a halogen atom; l is 0 to 2 (integer); m is 0 to 5 (integer); and l+m is an integer of 5 or less, with 4-hydroxyphenoxyalkanecarboxylic acid or its derivative having the formula

  (II)

wherein R represents hydrogen atom, a lower alkyl group of one to four carbon atoms, or a cation selected from the group consisting of sodium, potassium, magnesium, and calcium; and n is 0 or 2, in the presence of an alkaline compound selected from the group consisting of alkali metals, alkali metal hydroxides and alkali metal carbonates, in an aprotic polar solvent at a reaction temperature of 50° C. to the refluxing temperature, the molar ratio of the 4-hydroxyphenoxyalkanecarboxylic acid or its derivative to the 2-phenoxypyridine derivative being from 1 to 1.5, and the molar ratio of the alkaline compound to the 2-phenoxypyridine derivative being from 1 to 2.

2. A process according to claim 1 wherein the 2-phenoxypyridine derivative is a compound having the formula I wherein $X_1$ represents trifluoromethyl group; $X_2$ represents hydrogen or chlorine atom; Z represents chlorine atom; and Y, l and m are defined above.

3. A process according to claim 2 wherein the 2-phenoxypyridine derivative is a compound having the formula I wherein $X_1$ represents trifluoromethyl group; $X_2$ represents hydrogen atom; Z represents chlorine atom; l is 0 and m is an integer of 1 to 5 and Y is defined above.

4. A process according to claim 1 wherein said reaction is carried out at 70° to 120° C. in the presence of an alkali metal hydroxide or carbonate as said alkaline compound in an aprotic polar solvent, as said solvent.

* * * * *